United States Patent [19]

Chen et al.

[11] Patent Number: 4,557,673

[45] Date of Patent: Dec. 10, 1985

[54] IMPLANTABLE PUMP

[75] Inventors: Herbert Chen, Kensington; Michael G. Conley, El Cerrito, both of Calif.

[73] Assignee: Novacor Medical Corporation, Oakland, Calif.

[21] Appl. No.: 662,254

[22] Filed: Oct. 17, 1984

Related U.S. Application Data

[63] Continuation of Ser. No. 446,455, Dec. 3, 1982, abandoned.

[51] Int. Cl.[4] .................. F04B 43/00; F01B 19/00; F16J 3/00
[52] U.S. Cl. .................................. 417/412; 92/92; 128/1 D; 128/DIG. 3; 623/3
[58] Field of Search ................. 417/412, 413, 479; 92/98 D, 92; 3/1.7; 128/DIG. 3, 1 D

[56] References Cited

U.S. PATENT DOCUMENTS

| | | | |
|---|---|---|---|
| 1,893,776 | 1/1933 | Hull | 417/478 |
| 2,846,983 | 8/1958 | Otto | 92/98 D |
| 2,950,739 | 8/1960 | Lofink | 92/98 D |
| 4,167,046 | 9/1979 | Portner et al. | 417/412 X |
| 4,384,829 | 5/1983 | Conley et al. | 417/412 |

FOREIGN PATENT DOCUMENTS 482500  9/1975  Australia ..................... 3/1.7

*Primary Examiner*—Carlton R. Croyle
*Assistant Examiner*—Theodore W. Olds
*Attorney, Agent, or Firm*—Fitch, Even, Tabin & Flannery

[57] ABSTRACT

A chamber structure in a blood pump or the like is described. The structure includes a deformable sac having an annular side wall which is held in a rigid condition, and a pair of opposed circular walls, each joined to the annular side wall through a flexible annular wall portion. A circular pusher plate acting against each circular wall has an initial deflection position at which the associated flexible wall portion in the sac takes the form of a circumferentially uniform roll having an outwardly convex, bulged cross sectional curvature. The rolls in the sac maintain their circumferentially uniform, bulge-like character as the pusher plates are moved toward inwardly moved positions.

3 Claims, 5 Drawing Figures

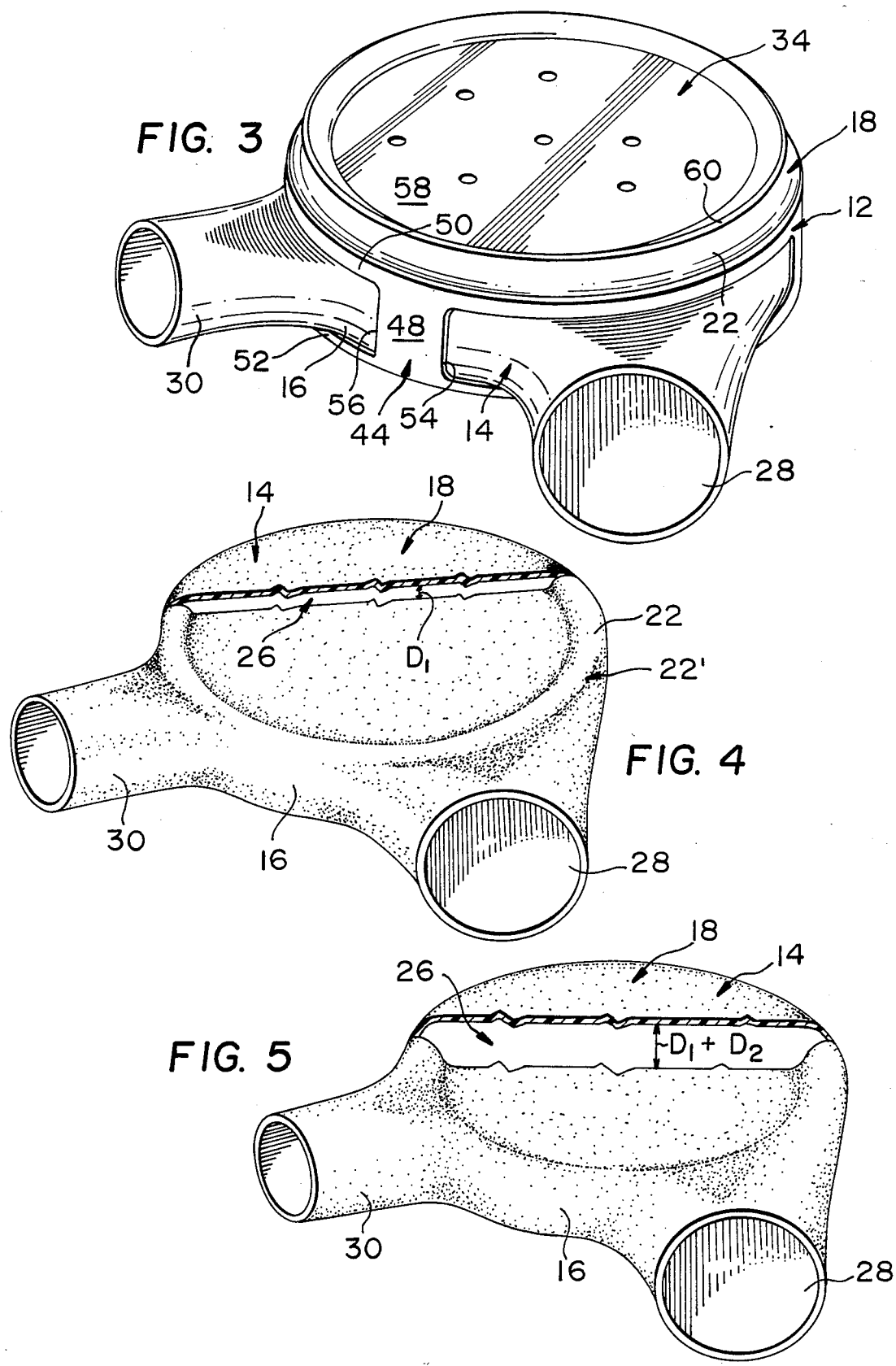

IMPLANTABLE PUMP

This is a continuation of application Ser. No. 446,455, filed Dec. 3, 1982, and now abandoned.

BACKGROUND AND SUMMARY

The present invention relates to an implantable pump, and more particularly to a fluid chamber structure in such a pump.

Efforts to produce heart-replacement and heart-assist devices have produced a variety of pump types and designs. One of these types is a deformable sac pump which operates by recurrent compression, or squeezing, of a deformable fluid chamber sac. A pump of this type typically consists of a disc-shaped deformable sac partially encased in a rigid housing, and an attached actuator used to compress the sac from opposite movable sides. The pump may be actuated pneumatically, by expanding and contracting fluids, by an electrical-actuated solenoid mechanism, by magnetic coupling to a driving magnet, or by other suitable driving mechanisms. The power source for the actuator is preferably external.

In any type of blood pump, the device must be constructed in size, shape and design to be readily implanted in a body cavity and to be comfortable over extended periods. The construction in the device must allow for efficient connections between the pump the vascular system near the heart. The pump must be highly reliable for long periods of continuous use. Specifically, the actuator mechanism in the pump must be efficient, long-lasting, and relatively smooth working. The chambered part of the pump—which in the case of a deformable-sac pump, includes the deformable sac itself—must be constructed to operate over long periods of continuous use with minimum stress-related fatigue and creasing. The sac design and operating characteristics must minimize thrombus formation in the fluid-containing portions of the pump. Additionally, the sac itself should be easy and relatively inexpensive to manufacture and incorporate into a rigid housing portion of the pump.

U.S. Pat. No. 4,167,046 discloses a deformable sac blood pump which solves or minimizes a number of problems associated with previously developed deformable sac blood pumps. The pump of that invention is composed of a disc-like deformable sac having an annular side wall and a pair of opposed circular walls which are adapted to be recurrently and sychronously moved toward one another, through the action of a pair of opposed pusher plates to produce pumping action. Inlet and outlet conduits in the sac are arranged to direct inlet and outlet flow substantially tangentially with respect to the annulus formed by the inner surface of the sac's annular side wall. The inlet and outlet conduits are disposed on either side of the pump region occupied by the pump actuator, producing a space-conserving arrangement of pump components. The sac itself is formed as a unitary seamless article from flexible resiliant material, providing a smooth interior sac surface which acts to prevent thrombus formation in the pump.

An object of the present invention is to provide in a deformable sac blood pump, a chamber structure which incorporates many of the advantageous features known in the prior art, including those of the pump described in the above-discussed patent, and which provides a number of unique and hitherto unknown features which enhance pump reliability and operational characteristics.

A more specific object of the invention is to provide in such a structure a deformable sac having flexing zones which are circumferentially uniform, preferably being entirely defined by machined elements.

A related object of the invention is to provide such a structure in which flexing of the sac during pump operation occurs primarily by a smooth rolling action in the flexing portions of the sac.

Yet another object of the invention is to provide such structure in which creasing and stress-related fatigue in the deformable sac are minimized.

Another object of the invention is to provide such structure designed to produce, during pumping operation a circular flow action which substantially reduces the degree of thrombus formation on inner sac surfaces.

It is still another object of the invention to provide such a chamber structure having a reduced thickness.

The novel chamber structure of the invention comprises, broadly, a deformable sac having an annular side wall which is held in a rigid condition, and a movable wall joined to the side wall through an outwardly convex flexible wall portion. A pusher plate acting against the movable wall has an initial deflection position at which the flexible wall portion takes the form of a circumferentially uniform, outwardly convex roll having a bulged cross sectional curvature. The roll maintains its circumferential uniformity and bulge-like character as the pusher plate is moved toward inwardly displaced positions to expel fluid from the sac.

In a preferred embodiment of the invention, the annular side wall is held in a rigid condition by attachment to curved inner wall portions of a rigid housing ring. The sac includes a pair of opposed, substantially parallel circular movable walls disposed on opposite sides of the housing ring, each wall being joined to the side wall by an outwardly convex flexible wall portion. A pair of pusher plates acting against associated circular walls are coordinately movable from such initial deflection positions to inwardly moved positions under the control of an actuator in the pump.

These and other objects and features of the present invention will become more fully apparent when the following detailed description of the invention is read in conjunction with the accompanying drawings.

A BRIEF DESCRIPTION OF THE DRAWINGS

FIG. 3 shows in perspective view, a chamber structure in the pump;

FIG. 4 is a perspective view like that of FIG. 3, with housing ring and pusher plate parts removed to show the condition of a deformable sac in the structure in a relaxed state (upper part of the figure) and in a start-of-stroke stroke condition (lower part of the figure); and FIG. 5 is a view like FIG. 4, but showing the sac in an end-of-stroke condition in the lower part of the figure.

DETAILED DESCRIPTION OF THE INVENTION

Figure 1:
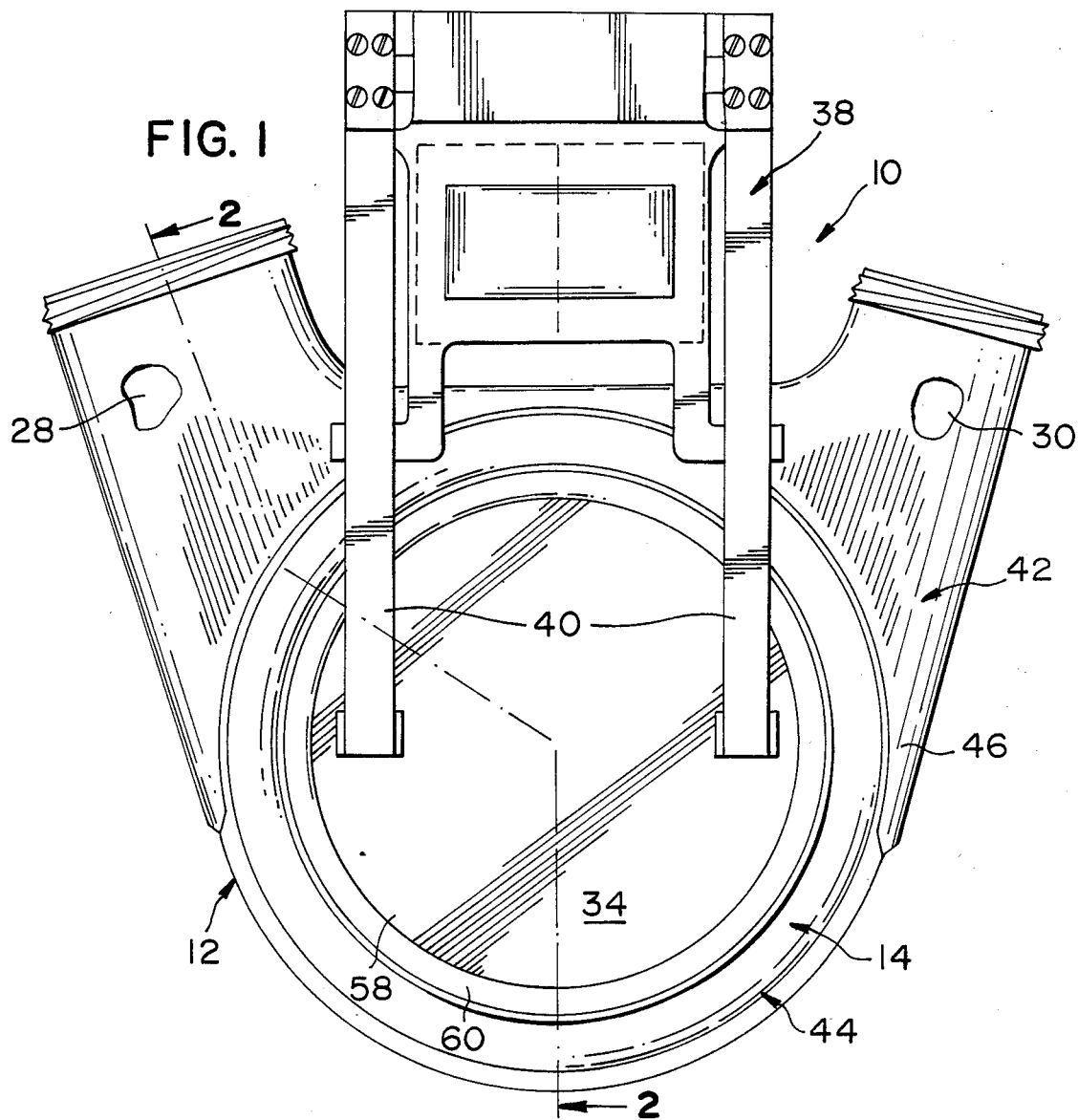
FIG. 1 is a somewhat schematic plan view, partially cutaway, of a blood pump constructed in accordance with the invention.

FIG. 1 shows a pump 10 constructed according to the present invention. The pump includes a chamber structure which is shown generally at 12 and whose components are shown removed from other parts of the pump in FIG. 3. Structure 12, whose construction and unique features will be described in greater detail below, includes a deformable sac 14 having an annular side wall 16, and a pair of opposed circular, movable walls 18, 20 (seen in FIG. 2) joined to the side wall through flexible curved wall portions 22, 24, respectively. These parts define a variable-volume annular sac chamber, or annulus, 26. Fluid is supplied to the annulus through an inlet conduit 28 and is expelled under pressure, through an outlet conduit 30.

The inlet and outlet conduits are provided with suitable valves, such as inlet valve 32 (FIG. 2), to produce the requisite one direction flow valving in the pump. Several clinical valves which are commercially available are suitable for use in the pump. In the particular embodiment illustrated herein, 29 mm and 27 mm porcine tissue valves are used in the inlet and outlet conduits, respectively.

A pair of opposed pusher plates 34, 36 (FIG. 2) attached to associated walls 18, 20, respectively, are movable inwardly, under the control of an actuator 38, to produce expulsion of fluid from the sac annulus. The actuator is mechanically connected to each pusher plate through connecting arms, such as arms 40 connecting the actuator to plate 34. Actuator 38, whose design forms no part of the present invention, is preferably an electrically powered solenoid-type actuator which functions to "close" opposed connecting arms coordinately and at a predetermined rate, to produce the desired pumping action in the pump.

Completing the description of what is shown generally in FIG. 1, pump 10 has a housing 42 which includes a rigid housing ring 44, to be described in detail below, and rigid shell 46 encasing the central region of structure 12, including ring 44. More particularly, the shell encases ring 44, the adjacent side wall region of sac 14, and is formed with passages which accomodate the inlet and outlet conduits in the sac.

The two valves in the pump are held in suitable fittings cast in the housing shell to anchor the valves in place in the deformable sac. The actuator is secured to the housing by suitable means to provide a rigid connection between the actuator and the nondeformable (side wall) portions of the pump sac. The entire pump structure just described may additionally be encased in a fluid tight outer housing (not shown) which is coated with a suitable bicompatible material.

Figure 2:
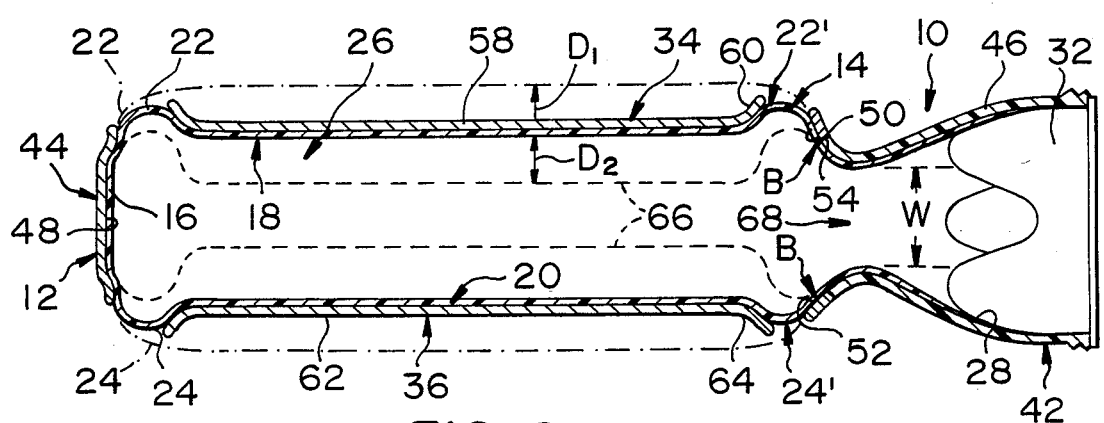
FIG. 2 is a sectional view taken generally along line 2—2 in FIG. 1.

Details of structure 12 will now be considered with particular reference to FIGS. 2-5. Referring first to FIGS. 2 and 3, ring 44 takes the form of an annular band having a subtantially straight-walled central portion 48 and a pair of circumferentially continuous annular lip portions 50, 52 having the inwardly curved cross sectional shape seen in FIG. 2. A pair of slots 54, 56 (FIG. 3) formed in the ring accomodate inlet and outlet conduits in the sac, respectively. Each slot extends about an approximately 90° arc, with the width of each slot corresponding approximately to the width of the central wall portion in the ring. That is, each slot extends in width substantially between the two opposed annular lip portions in the housing ring. The ring is preferably formed from a lightweight corrosion-resistant material, such as titanium, or a strong rigid polymeric material or the like. The inner surfaces of the curved lip portions in the ring are preferably machined or molded surfaces, for a purpose to be described.

With continued reference to FIGS. 2 and 3, plate 34, which is representative, includes a circular, substantially planar portion 58, and a curved annular lip portion 60 having the cross-sectional curvature seen in FIG. 2. Plate 36 likewise has a circular planar portion 62 bordered by an annular curved lip portion 64. The pusher plates are preferably formed of a lightweight corrosion-resistant material such as titanium, or of a strong, rigid fiber composite. The inner surfaces of the lip portions in the two pusher plates, like the inner surfaces of the lip portions in the housing ring, are preferably machined or molded, also for a purpose to be described.

While not shown in FIGS. 2 and 3, the pusher plates include mounting structure through which the associated connecting arms, such as arms 40, are attached to the associated plates, as can be appreciated with reference to FIG. 1. According to an important feature of the present invention, the two plates are movable, under the control of actuator 38, acting through the connecting arms, from axially symetric initial deflection positions, shown in solid lines in FIG. 2, toward inwardly moved positions. The positions of the inner surfaces of the sac at the end-of-stroke pusher plate positions are shown in dashed lines at 66 in FIG. 2.

Considering details of sac 14, inlet and outlet conduits 28, 30, respectively, communicate with the sac annulus through elongate ports, such as inlet port 68 (FIG. 2), formed in the sac. As seen in FIG. 2, port 68, which is representative, is defined cross-sectionally by a pair of confronting, inwardly convex rolling surfaces which join the annulus and conduit sides of the sac, defining a minimum flow area of width denoted at W in FIG. 2. Each port, such as port 68, is substantially coextensive, in an arcuate direction, with the corresponding housing ring slot, such as slot 54, through which that part of the sac extends. An advantage of this construction is that a port having a relatively large fluid passage area is formed in an anchored, stationary side wall portion of the sac, whereby the shape of the port is substantially constant during pump operation.

Sac 14 is formed as a unitary seamless article from flexible resiliant, blood compatible material. This material may be of any type suitable for pumping blood, such as certain types of polyurethanes. The material of which the sac is comprised should have long-term retention of physical strength under combined dynamic stressing and hydrolysis. The material should be of low toxicity and long-term stability for compatability with blood. The material should also be of high strength, be capable of being repeatedly flexed, be capable of being sterilized and be easily fabricated. Suitable materials are linear segmented polyurethanes, for example BIOMER from Ethicon.

One preferred method of making the sac comprises successively coating an accurately machined and polished aluminum mandrel whose outer surfaces define the inner surfaces of the sac. Since both of the opposed annular flexible portions in the sac are circumferentially uniform, the surfaces of the mandrel forming such flexible surfaces can be accurately machined, polished, and coated to produce extremely regular and smooth surfaces. To form the sac, the coated mandrel is repeatedly dipped in the selected polymer solution and dried with rotation under infrared lamps. The dipping and drying steps are preferably performed under low humidity conditions. After dipping, the sac is annealed in a vacuum oven. The sac is washed thoroughly in distilled water, solvent extracted and dried in a vacuum oven.

Referring to FIG. 2, the sac is fitted within ring 44, and flexible sac portions are attached, as with adhesives, to confronting ring lip portions in the region of the ring slots 54, 56. The opposed circular walls in the sac are attached, by a suitable adhesive or the like, to the circular plate portion in the associated pusher plate. The flexing zones of the sac which are not bonded to either the pusher plate or the housing ring are coated with a release agent.

Sac 14 in a relaxed, "as cast" condition, has the general shape seen at the top in FIGS. 4 and 5. In this condition, the circular walls and associated sac flexible portions have the cross sectional curvature seen in dash-dot lines in FIG. 2. According to an important feature of the invention, the pusher plates in the pump are placed at symetrical, initial deflection positions, seen in solid lines in FIG. 2, at which the circular walls have been moved inwardly toward one another a distance indicated at $D_1$ in the figure. In the particular pump embodiment being described, $D_1$ is preferably about 5.1 mm.

With plates 34, 36 in their initial deflection positions, the associated flexible wall portions in the sac assume the form of circumferentially uniform, outwardly convex rolls, each having the bulged cross sectional curvature seen in solid lines in FIG. 2. The rolls formed in wall portions 22, 24 are denoted at 22', 24', respectively in FIG. 2. It can be appreciated in this figure that the radius of curvature of each roll is substantially less than that of the flexible wall when the sac is in its relaxed condition.

In operation, the two pusher plates are moved, under the control of actuator 38, coordinately and at desired displacement rates, inwardly toward one another from their initial deflection positions toward end-of-stroke positions which place the inner surfaces of the interior of the sac at the positions indicated by tthe two dashed lines 66 in FIG. 2. The total working stroke, or distance that each plate is moved, is denoted $D_2$ in FIGS. 2 and 5. In the particular embodiment herein, $D_2$ is about 6.4 mm.

Movement of the pusher plates from their initial deflection positions inwardly is accomodated by a smooth rolling action of the inner and outer annular regions of each roll against the lip portions in the associated pusher plate and housing ring. The sac-to-housing bond lines in the slot regions of the housing ring, indicated at B in FIG. 2, are located at the point where the sac roll is tangential to the associated housing ring lip portion at the end-of-stroke position. According to an important feature of the invention, and as can be appreciated with reference to FIGS. 2, 4 and 5, each roll in the sac remains circumferentially uniform and bulged in cross sectional curvature as the pusher plates are moved inwardly from their initial deflection positions. As noted above, the ports communicating the inlet and outlet conduits with the sac annulus are formed entirely within the portion of the sac attached to ring 44. Consequently, the flexing action in the sac occurs substantially independently of, and without effect on, the shape of the ports.

The pusher plates are moved back to their initial deflection position either under the control of the actuator, or passively by inflow of fluid, such as from heart pumping. Sac expansion is accomodated by a smooth, circumferetially uniform rolling action in the sac rolls which characterizes movement of the two rolls during sac contraction.

In flow visualization studies conducted with a pump having clear pusher plates, it was observed that during pump expansion, a circular flow pattern was established which acted to evenly wash the interior surfaces of the sac. In particular, a portion of the flow in the sac is directed back into the inflow conduit to wash the inflow valve. The circular, diastolic flow pattern was very well established and existed until early systole. The improved washing in the valve regions of the pump is due in part to the fact that the inflow conduit is relatively short. The fact that both conduits communicate with the sac annulus through elongate ports whose widths and lengths are substantially fixed during sac contraction and expansion also promotes washing and tangential flow between the conduit regions and the sac annulus.

Analysis of the stress characteristic in the operating pump indicate that the pump design provides a number of improved stress characteristics. Sac stresses were found to be comparable to those in earlier-developed pumps, particularly that described in U.S. Pat. No. 4,167,046. However, the stresses in the instant pump are more repeatable and predictable due to the fact that flexing occurs in a region of the deformable sac defined by machined or molded components, this region being itself formed on machined surfaces in the mandrel.

Reduced tendency of the flexing zones to crease is another important feature of the invention. Generally, for a given sac thickness and pusher-plate diameter, the factors which lead to crease formation are long working strokes, and a large housing-to-pusher plate separation. One advantage of the present invention is that due to the predeflection of the pusher plates, the total working stroke in the pump is only about 60% of the total allowed deflection in the sac. Studies on crease formation indicate that, at the pusher plate-housing ring clearance selected, the working stroke in the pump is at least about 10% less than that which can lead to creasing.

From the above, it can be seen how the present invention provides improved operation and reliability in a deformable sac type blood pump. The two annular flexing zones in the pump are each circumferentially uniform and defined by annular machined or molded components to increase stability and circular flow characteristics. The predeflection feature in the pump functions to create a bulged annular roll in each of the flexing zones, which can accomodate recurrent sac wall movement by a smooth rolling action that minimizes localized stresses and the tendency to crease over extended operation.

The predeflection feature in the pump produces two other significant advantages. First, the thickness of the pump chamber structure, with such in a filled, start-of-stroke condition, is considerably reduced over the thickness the structure would have with the sac in a fully expanded condition. The reduced thickness is two times $D_1$, or about 10 mm in the particular pump described herein. The advantage of the reduced pump thickness in an implantable pump can be appreciated. Secondly, a relatively small internal volume in the pump chamber, at the end of stroke, can be achieved with a relatively small total stroke. The small internal volume promotes "flushing" of fluid from the pump, thereby reducing the potential for thrombus formation.

The problem of thrombus formation in the sac is reduced both by the improved flow characteristics which are observed during pump operation, and by the features of the sac construction which promote washing in the conduit regions of the sac. In this regard, the elongate ports communicating the conduits with the annulus in the sac and the relatively short inflow valve are important.

While a preferred embodiment of the invention has been described herein, it will be evident to those skilled in the art that various changes and modifications may be made without departing from the spirit of the invention. In particular, the invention also contemplates an asymetric chamber structure in which pumping occurs through movement of a single wall, where such movement is accomodated by the rolling action of a circumferentially uniform bulged roll, as described.

The invention also contemplates a sac which is formed to have, in a relaxed, or unstressed, condition, the general cross-sectional shape seen in solid lines in FIG. 2. That is, the sac, as cast, is formed to have a pair of opposed recessed circular walls bordered by a circumferentially uniform roll having a bulged cross sectional curvature. The sac may also be constructed to have an annular side wall which is, by its construction, inherently rigid and therefore does not require external rigidifying structure, such as the housing ring described.

What is claimed is:

1. Chamber structure in a blood pump comprising a deformable seamless sac having a variable volume defined by an annular side wall and a pair of generally circular movable walls each joined to said side wall along opposite annular edges thereof through an outwardly convex flexible wall portion, said sac including inlet and outlet curved elongated ports each communicating with the sac and being defined by the inner surface of said side wall, said ports being disposed to direct inlet and outlet flow through said sac, pusher means including a pair of opposed reciprocally acting pusher plates acting against said movable walls and being adapted for movement toward each other from an initial deflection position, at which said flexible wall portions each takes the form of a circumferentially uniform roll having an outwardly bulged cross-sectional curvature, toward an end-of-stroke position, said rolls each maintaining its circumferentially uniform bulge-like character throughout said movement, a housing which includes a shell having inlet and outlet conduits surrounding said inlet and outlet ports and a rigid housing ring defining an annular wall surface exending around the outside of said side wall of said sac, said housing ring having elongated slots through which project said elongated ports of said sac, said housing ring and said pusher plates defining curved annular lip portions adapted to accommodate rolling of associated inner and outer edge regions, respectively, in said rolls as said pusher plates are moved toward each other from their initial deflection positions, said inlet and outlet conduits having curving surfaces extending from said curving annular lip portions of said housing ring, said curved annular lip portions of said housing ring and said pusher plates being curved and flared to present curved inner surfaces for rolling engagement with said sac, said sac being bonded to said annular wall surface of said housing ring and to said housing ring adjacent said elongated slots to hold said sac ports against change in cross section during the flexing of said sac, said outer portions of said curved annular lip portions of said housing ring being unattached to said outwardly convex flexible wall portions of said sac to allow the latter to have a smooth rolling action without creasing along said outer portions during sac contraction and expansion, said pusher plates having a selected total working stroke between the initial deflection position and the end-of-stroke position, and said pusher plate and said housing having a selected ring clearance, such that the interior surface of said sac remains essentially crease-free throughout the working stroke of the pump, said rigid housing ring having sac-to-housing bond lines located such that the roll in said sac adjacent thereto is substantially tangential to said annular lip portions of said housing ring throughout movement of said pusher plates between said initial deflection position and said end-of-stroke positions.

2. The structure of claim 1, wherein the spacing between said conduits is movable walls is within the range in a substantially relaxed condition is greater than said spacing in their extended deflection position.

3. The structure of claim 1, wherein such said ring gets closer to said housing ring extends for a limited distance of said housing ring within a circumferential direction substantially about continuous degrees of arc.